(12) United States Patent
Luo et al.

(10) Patent No.: US 11,374,179 B2
(45) Date of Patent: Jun. 28, 2022

(54) DITHIAZINE-BASED HOLE TRANSPORT MATERIAL, PREPARING METHOD THEREOF, AND ORGANIC LIGHT-EMITTING DEVICE

(71) Applicant: Wuhan China Star Optoelectronics Semiconductor Display Technology Co., Ltd., Wuhan (CN)

(72) Inventors: Jiajia Luo, Wuhan (CN); Xianjie Li, Wuhan (CN); Jinchang Huang, Wuhan (CN); Yu Gu, Wuhan (CN); Lin Yang, Wuhan (CN); Yamei Bai, Wuhan (CN)

(73) Assignee: Wuhan China Star Optoelectronics Semiconductor Display Technology Co., Ltd., Wuhan (CN)

( * ) Notice: Subject to any disclaimer, the term of this patent is extended or adjusted under 35 U.S.C. 154(b) by 0 days.

(21) Appl. No.: 16/615,850

(22) PCT Filed: Sep. 20, 2019

(86) PCT No.: PCT/CN2019/107096
§ 371 (c)(1),
(2) Date: Nov. 22, 2019

(87) PCT Pub. No.: WO2021/017122
PCT Pub. Date: Feb. 4, 2021

(65) Prior Publication Data
US 2022/0149297 A1   May 12, 2022

(30) Foreign Application Priority Data
Jul. 30, 2019 (CN) .......................... 201910694424.5

(51) Int. Cl.
*H01L 51/00* (2006.01)
*C07D 495/04* (2006.01)
*H01L 51/50* (2006.01)

(52) U.S. Cl.
CPC ........ *H01L 51/0074* (2013.01); *C07D 495/04* (2013.01); *H01L 51/0072* (2013.01); *H01L 51/5056* (2013.01); *H01L 2251/552* (2013.01)

(58) Field of Classification Search
CPC ............ H01L 51/0074; H01L 51/0072; H01L 51/5056; H01L 2251/552; C07D 495/04
See application file for complete search history.

(56) References Cited

U.S. PATENT DOCUMENTS

| | | | |
|---|---|---|---|
| 3,885,044 A | 5/1975 | Beck | |
| 2013/0320307 A1* | 12/2013 | Birnstock | H01L 51/5268 257/40 |

FOREIGN PATENT DOCUMENTS

| | | |
|---|---|---|
| CN | 102317406 A | 1/2012 |
| CN | 104844587 A | 8/2015 |

(Continued)

OTHER PUBLICATIONS

Electrochemical Activity of Sulfur-Linked Tetraionaphthalene Polymer, Journal of The Electrochemical Society, Tomoo Sarukawa et al., Dec. 9, 2009.

*Primary Examiner* — Shane Fang
(74) *Attorney, Agent, or Firm* — Nathan & Associates; Menachem Nathan

(57) ABSTRACT

A dithiazine-based hole transport material, preparing method thereof and an organic light-emitting device are provided; a molecular structural formula of the hole transport material is as following:

(Continued)

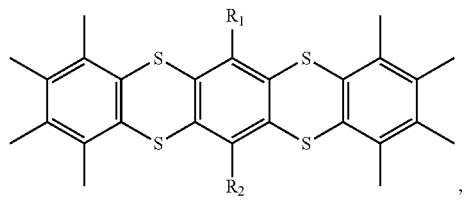

wherein R₁ and R₂ are each an electron-donating group.

5 Claims, 1 Drawing Sheet

(56) References Cited

FOREIGN PATENT DOCUMENTS

| | | |
|---|---|---|
| CN | 108218891 A | 6/2018 |
| CN | 108299449 A | 7/2018 |
| CN | 108359443 A | 8/2018 |
| CN | 109096246 A | 12/2018 |
| CN | 109535013 A | 3/2019 |
| JP | H01228993 A | 9/1989 |
| KR | 20190063717 A | 6/2019 |

\* cited by examiner

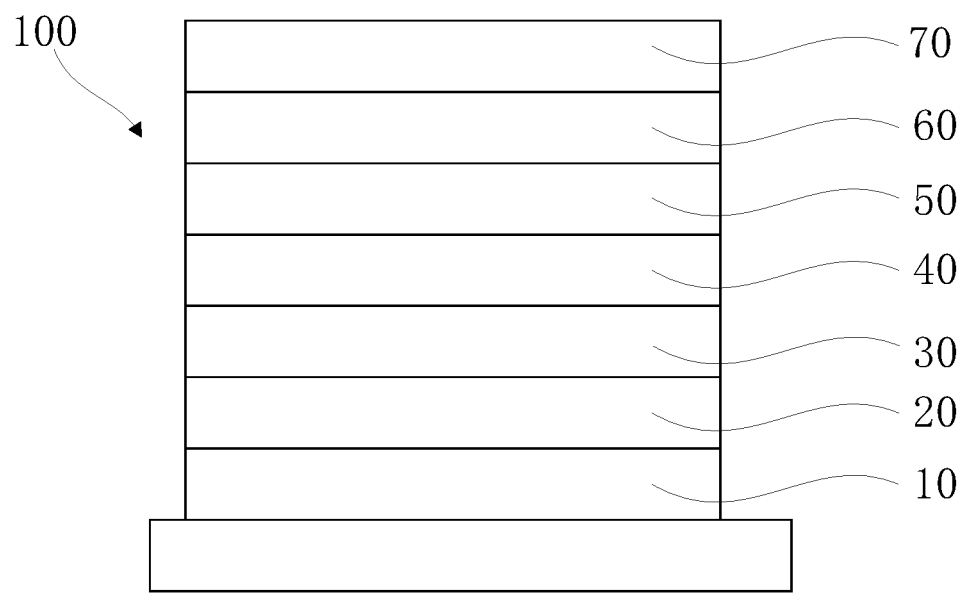

DITHIAZINE-BASED HOLE TRANSPORT MATERIAL, PREPARING METHOD THEREOF, AND ORGANIC LIGHT-EMITTING DEVICE

FIELD OF INVENTION

The present disclosure relates to the field of organic optoelectronic materials, and more particularly to a dithiazine-based hole transport material, preparing method thereof and an organic light-emitting device.

BACKGROUND OF INVENTION

The description herein merely provides background information related to the present disclosure and does not necessarily constitute prior art.

Organic light-emitting diodes (OLEDs) have advantages of active illumination without backlight, high luminous efficiency, wide viewing angles, fast response times, large temperature adaptation ranges, simple production and processing, low driving voltages, low energy consumption, lighter, thinner, able to realize flexible displays and wide application prospect, thereby drawing attention of many researchers.

According to the functions, materials of an OLEDs device can be divided into a hole injection material, a hole transport material, a hole blocking material, a light-emitting host material, a light-emitting guest material, an electron injection material, an electron transport material, an electron blocking material, a metal cathode and a photocoupler output material. For current top-emitting OLEDs devices, the hole transport material as the thickest layer (the largest consumption of mass production materials), there is a contradiction between energy levels and hole mobilities. Therefore, there is an urgent need to develop a hole transport material with matching energy levels and high mobilities.

SUMMARY OF INVENTION

The present disclosure provides a dithiazine-based hole transport material, preparing method thereof and an organic light-emitting device. The present disclosure provides a hole transport material with matching energy levels and high mobilities by combining a relatively coplanar dithiazine having strong electron-donating abilities with other electron-donating groups.

To solve the above problem, the present disclosure provides following technical solutions:

An embodiment of the present disclosure provides a dithiazine-based hole transport material. The dithiazine-based hole transport material comprises a molecular structural formula as following:

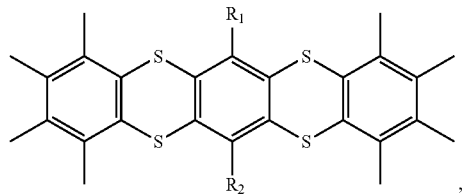

wherein R1 and R2 are each an electron-donating group.

In an embodiment of the present disclosure, wherein R1 and R2 are each a carbazolyl group and derivatives thereof, a diphenylamino group and derivatives thereof, a phenazine group and derivatives thereof, an acridine group and derivatives thereof, or a five-membered or six-membered heterocyclic aromatic group having one or more hetero atoms selected from the group consisting of N, O and Si.

In an embodiment of the present disclosure, wherein R1 and R2 are each a substituted or unsubstituted dialkylamino group, substituted or unsubstituted alkylamino group, substituted or unsubstituted amino group, substituted or unsubstituted alkoxy group, substituted or unsubstituted amide group, substituted or unsubstituted acyloxy group, substituted or unsubstituted alkyl group, substituted or unsubstituted carboxymethyl group, substituted or unsubstituted phenyl group or hydroxyl group; wherein the substituted group is an alkyl group or halogen.

In an embodiment of the present disclosure, wherein R1 and R2 are each a structural formula selected from the group consisting of following structural formulas:

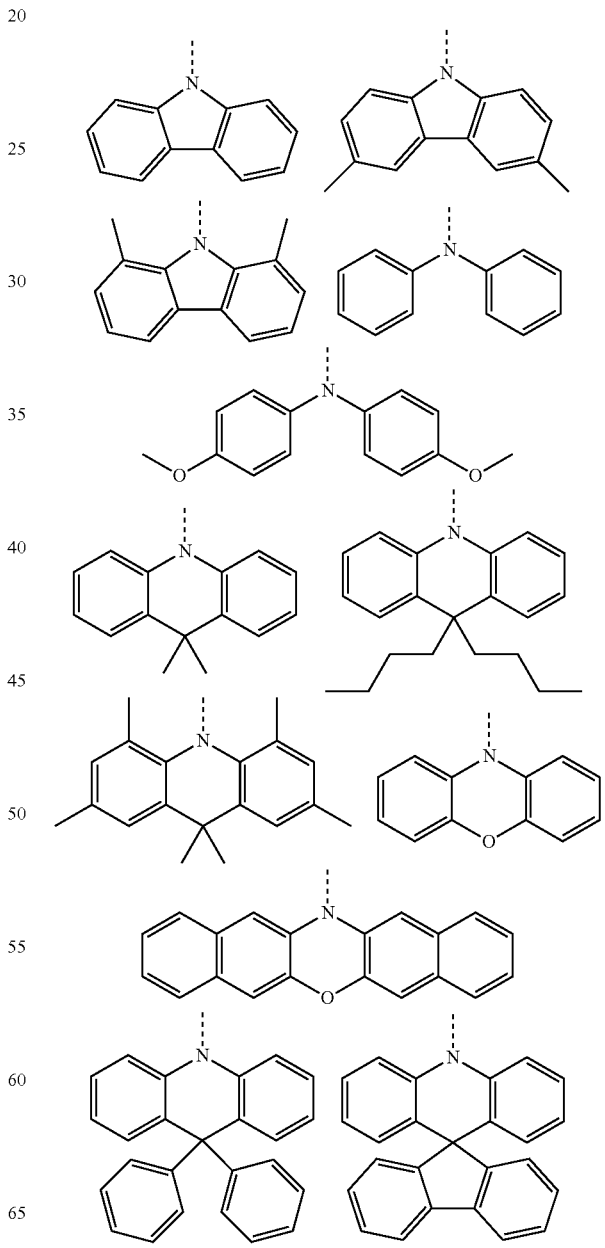

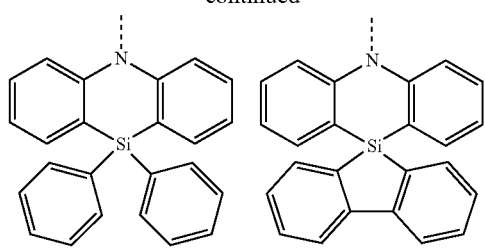
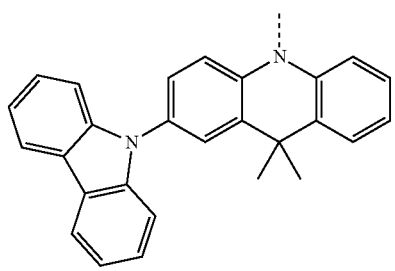
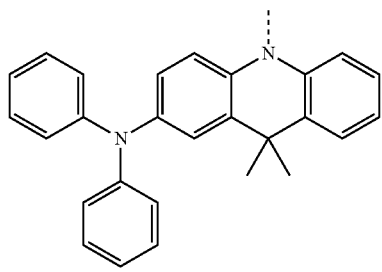
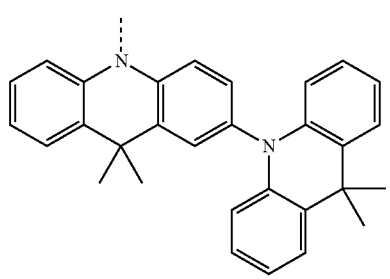
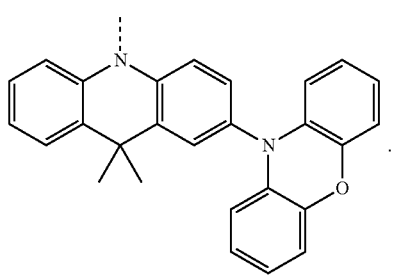
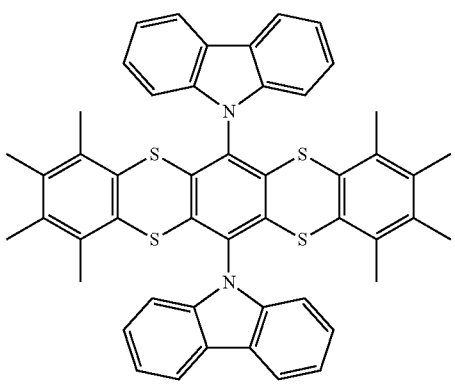
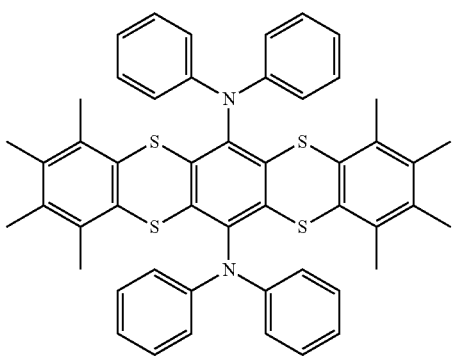
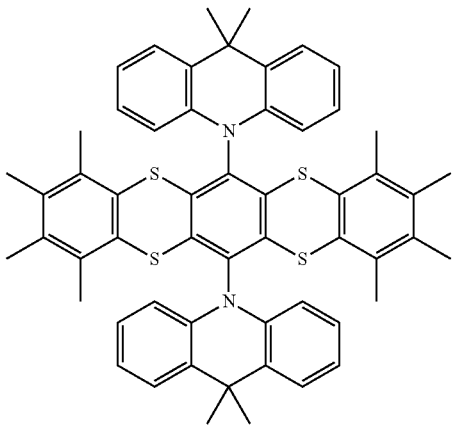
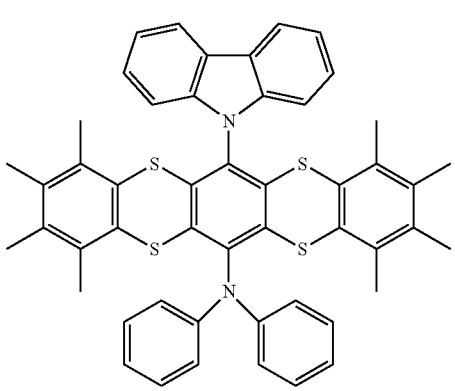
In an embodiment of the present disclosure, wherein R1 and R2 are the same.
In an embodiment of the present disclosure, a molecular structural formula of the dithiazine-based hole transport material is selected from the group consisting of following structural formulas:

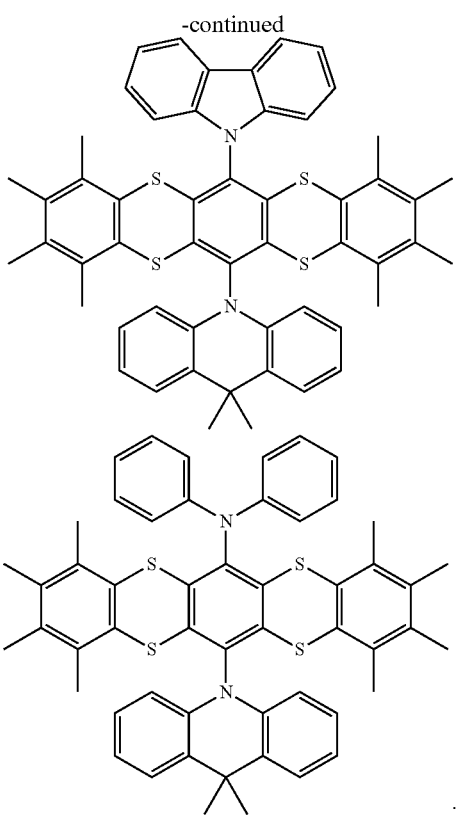

An embodiment of the present disclosure further provides a preparing method of the dithiazine-based hole transport material, comprising following steps:

a compound containing dithiazine reacting with hydrides of R1 and R2 and catalyzed by a palladium catalyst and tri-tert-butylphosphine tetrafluoroborate in an organic solvent containing an alkaline alkoxide to obtain the dithiazine-based hole transport material; wherein a molecular structural formula of the compound containing dithiazine is as following:

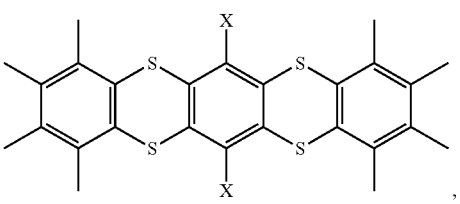

wherein X is chlorine, bromine, iodine, or astatine.

In the preparing method of the dithiazine-based hole transport material according to an embodiment of the present disclosure, the step of a compound containing dithiazine reacting with hydrides of R1 and R2 and catalyzed by a palladium catalyst and tri-tert-butylphosphine tetrafluoroborate in an organic solvent containing an alkaline alkoxide to obtain the dithiazine-based hole transport material, comprises following steps:

the compound containing dithiazine reacting with a hydride of R1 and catalyzed by a palladium catalyst and tri-tert-butylphosphine tetrafluoroborate in an organic solvent containing an alkaline alkoxide to obtain an intermediate product; and the intermediate product reacting with a hydride of R2 and catalyzed by the palladium catalyst and tri-tert-butylphosphine tetrafluoroborate in the organic solvent containing an alkaline alkoxide to obtain the dithiazine-based hole transport material; wherein a molecular structural formula of the intermediate product is as following:

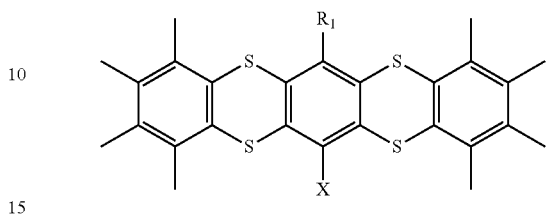

In the preparing method of the dithiazine-based hole transport material according to an embodiment of the present disclosure, the alkaline alkoxide comprises sodium tert-butoxide or potassium tert-butoxide.

In the preparing method of the dithiazine-based hole transport material according to an embodiment of the present disclosure, the organic solvent comprises toluene.

In the preparing method of the dithiazine-based hole transport material according to an embodiment of the present disclosure, the palladium catalyst comprises palladium acetate.

In the preparing method of the dithiazine-based hole transport material according to an embodiment of the present disclosure, wherein R1 and R2 are each a carbazolyl group and derivatives thereof, a diphenylamino group and derivatives thereof, a phenazine group and derivatives thereof, an acridine group and derivatives thereof, or a five-membered or six-membered heterocyclic aromatic group having one or more hetero atoms selected from the group consisting of N, O and Si.

In the preparing method of the dithiazine-based hole transport material according to an embodiment of the present disclosure, wherein R1 and R2 are the same.

An embodiment of the present disclosure further provides an organic light-emitting device, the organic light-emitting device comprises an anode, a hole injection layer, a hole transport layer, a light-emitting layer, an electron transport layer, an electron injection layer and a cathode disposed in sequence; wherein a material of the hole transport layer comprises the above dithiazine-based hole transport material.

In the organic light-emitting device according to an embodiment of the present disclosure, wherein R1 and R2 are each a carbazolyl group and derivatives thereof, a diphenylamino group and derivatives thereof, a phenazine group and derivatives thereof, an acridine group and derivatives thereof, or a five-membered or six-membered heterocyclic aromatic group having one or more hetero atoms selected from the group consisting of N, O and Si.

In the organic light-emitting device according to an embodiment of the present disclosure, wherein R1 and R2 are the same.

In the organic light-emitting device according to an embodiment of the present disclosure, a molecular structural formula of the dithiazine-based hole transport material is selected from the group consisting of following structural formulas:

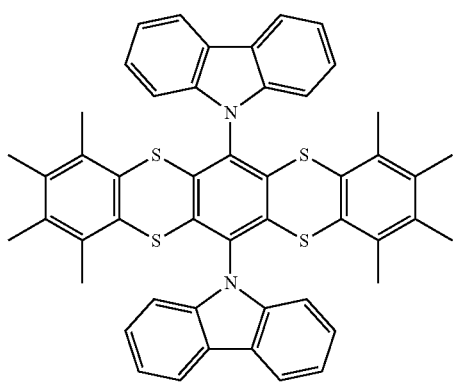
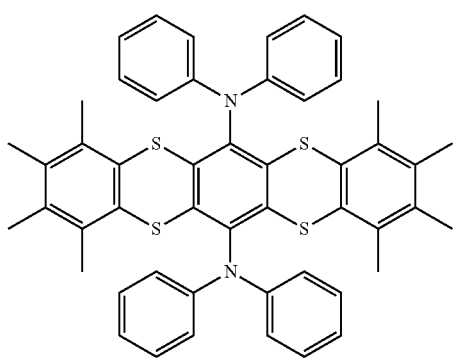
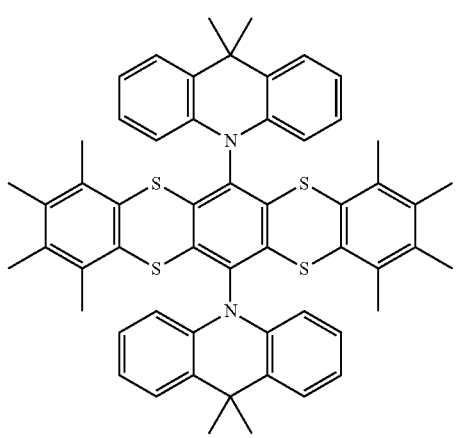
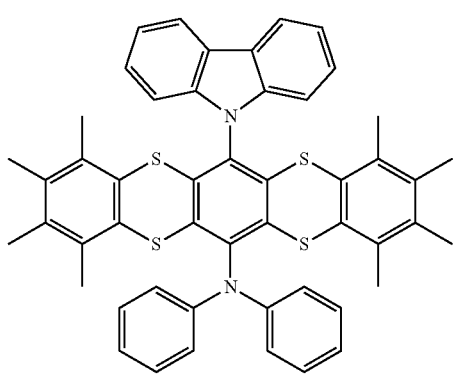
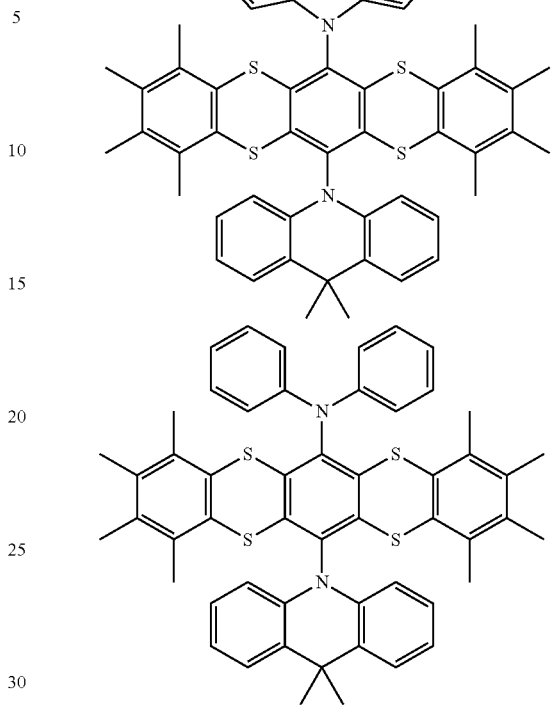

-continued

The beneficial effect of the present disclosure is: the present disclosure provides a dithiazine-based hole transport material. Dithiazine is favorable to obtain a hole transport material with suitable HOMO/LUMO energy levels due to its strong electron-donating abilities and having a relatively coplanar structure, and dithiazine combining other electron-donating groups R1 and R2 can obtain a hole transport material having higher hole mobilities. It can be known from the experimental data, the HOMO energy level of the dithiazine-based hole transport material in the present disclosure can achieve about −5.6 eV which matches the HOMO energy level of a P-type doped hole transport material.

DESCRIPTION OF DRAWINGS

The accompanying FIGURES to be used in the description of embodiments of the present disclosure or prior art will be described in brief to more clearly illustrate the technical solutions of the embodiments or the prior art. The accompanying FIGURES described below are only part of the embodiments of the present disclosure, from which FIGURES those skilled in the art can derive further FIGURES without making any inventive efforts.

FIG. 1 is a schematic structural diagram of an organic light-emitting device according to an embodiment of the present disclosure.

DETAILED DESCRIPTION OF PREFERRED EMBODIMENTS

To more clearly illustrate the present disclosure, the embodiments of the present disclosure are described in detail hereinafter, but are not limited thereto.

Embodiment 1

An embodiment of the present disclosure provides a dithiazine-based hole transport material. The dithiazine-based hole transport material comprises a molecular structural formula as following:

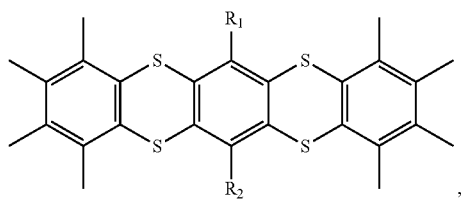

wherein R1 and R2 are each an electron-donating group.

Specifically, R1 and R2 are each a carbazolyl group and derivatives thereof, a diphenylamino group and derivatives thereof, a phenazine group and derivatives thereof, an acridine group and derivatives thereof, or a five-membered or six-membered heterocyclic aromatic group having one or more hetero atoms selected from the group consisting of N, O and Si. For example, R1 and R2 are each a structural formula selected from the group consisting of following structural formulas:

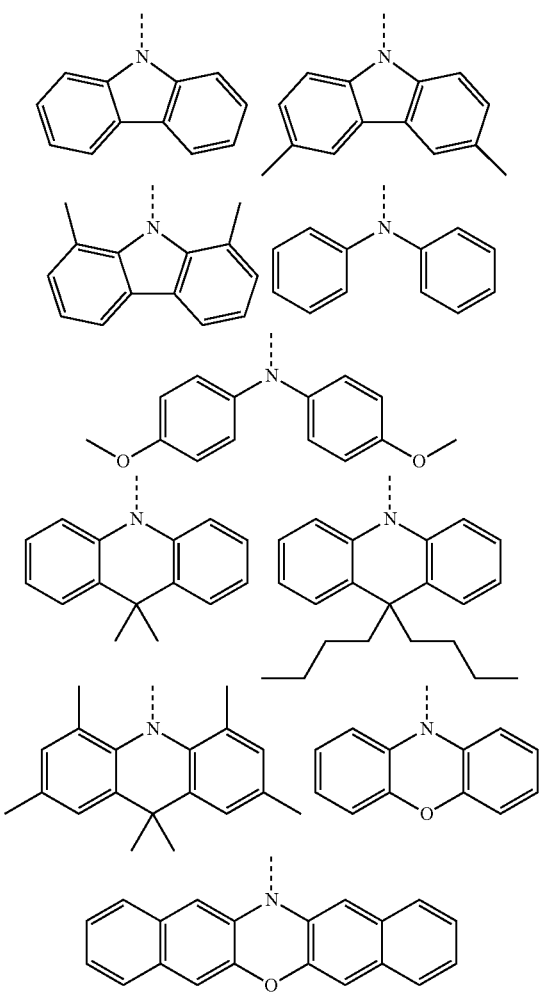

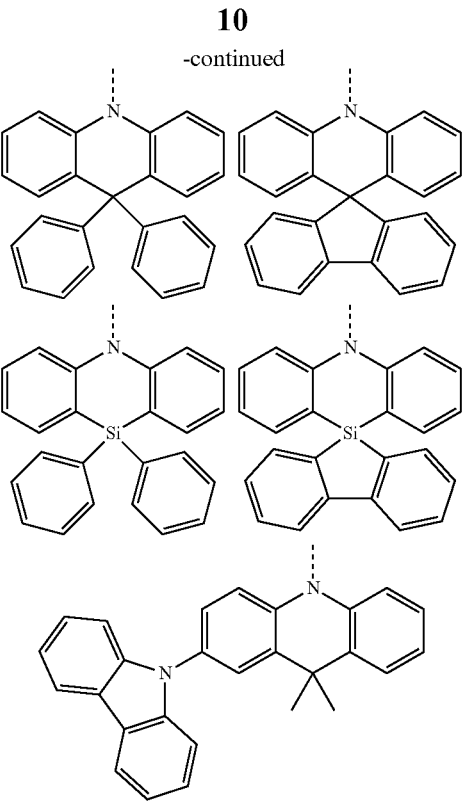

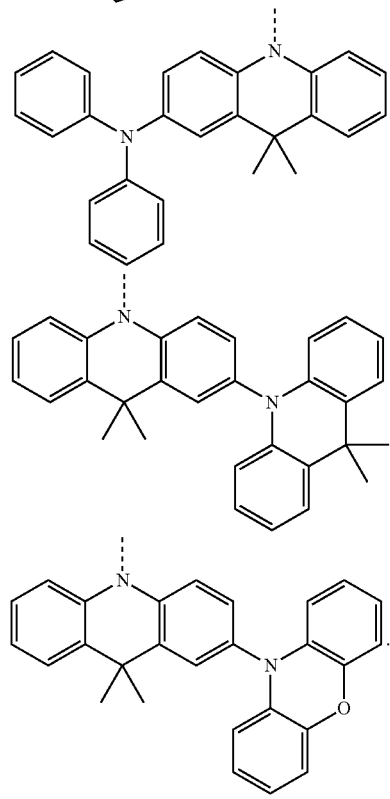

Specifically, R1 and R2 are each a substituted or unsubstituted dialkylamino group, substituted or unsubstituted alkylamino group, substituted or unsubstituted amino group, substituted or unsubstituted alkoxy group, substituted or unsubstituted amide group, substituted or unsubstituted acyloxy group, substituted or unsubstituted alkyl group, substituted or unsubstituted carboxymethyl group, substituted or unsubstituted phenyl group or hydroxyl group; wherein the substituted group is an alkyl group or halogen.

Specifically, R1 and R2 can be the same or different.

In an embodiment of the present disclosure, dithiazine is favorable to obtain a hole transport material with suitable HOMO/LUMO energy levels due to its strong electron-donating abilities and having a relatively coplanar structure, and dithiazine combining other electron-donating groups R1 and R2 can obtain a hole transport material having higher hole mobilities.

Embodiment 2

An embodiment of the present disclosure provides a dithiazine-based hole transport material, a molecular structural formula of the dithiazine-based hole transport material is as following:

Compound 1

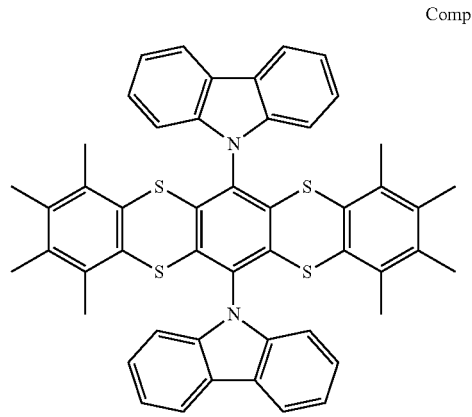

Compound 2

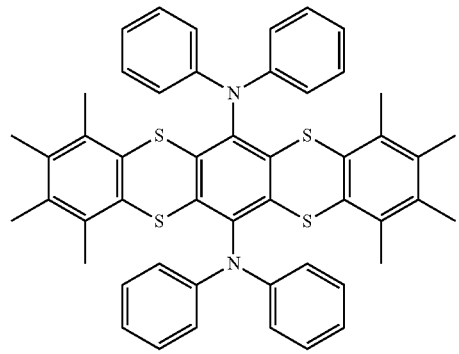

Compound 3

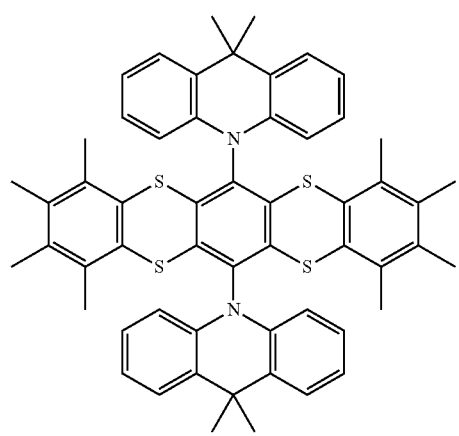

Compound 4

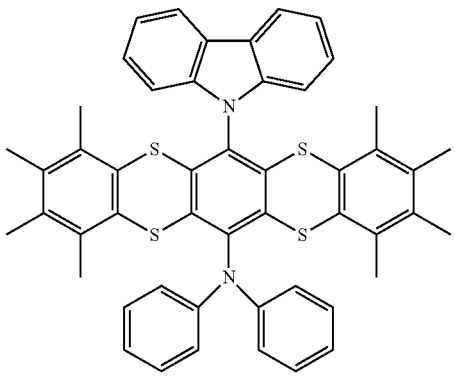

Compound 5

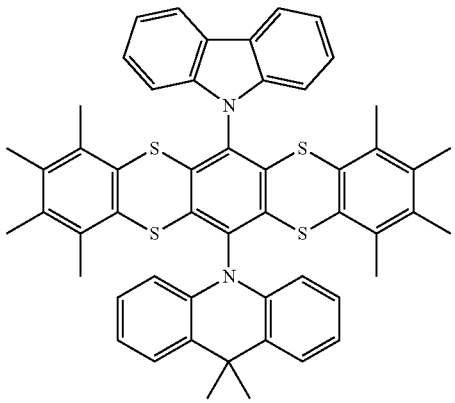

Compound 6

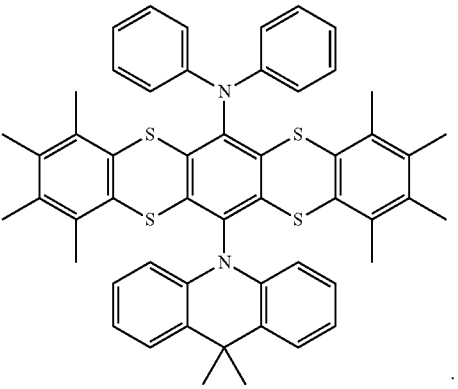

All the six compounds provided in the embodiment have dithiazine structures. The above six compounds can be a hole transport material having suitable HOMO/LUMO energy levels due to strong electron-donating abilities and a relatively coplanar structure of dithiazine; carbazolyl group, diphenylamino group and 9,9'-dimethyl acridine group which combined with the dithiazine structure are electron-donating groups that make the hole transport materials of above six compounds have higher hole mobilities.

Embodiment 3

The Preparing Method of Compound 1:

Add raw materials (3.11 g, 5 mmol), carbazole (2.00 g, 12 mmol), palladium acetate (Pd(OAc)2, 180 mg, 0.8 mmol) and tri-tert-butylphosphine tetrafluoroborate ((t-Bu)

3HPBF4, 0.68 g, 2.4 mmol) to a 250 mL two-necked flask, and then add sodium tert-butoxide (NaOt-Bu, 1.16 g, 12 mmol) to the two-necked flask in a glove box. Under an argon atmosphere, add 100 mL toluene which removes water and oxygen to the two-necked flask and react at 120° C. for 48 hours. After the reaction, cool the obtained reaction solution to room temperature and then pour the reaction solution into a 200 mL of ice water. The product is extracted from dichloromethane at least three times, combined with the organic phase, spun into silica gel, and then purified by column chromatography (volume ratio of dichloromethane and n-hexane is 1:4) to obtain a white powdery product (2.9 g, yield rate: 73%). The white powdery product confirmed by mass spectrometry (MS (EI) m/z: [M]+: 796.10) is Compound 1.

Wherein the preparation route of Compound 1 is as following:

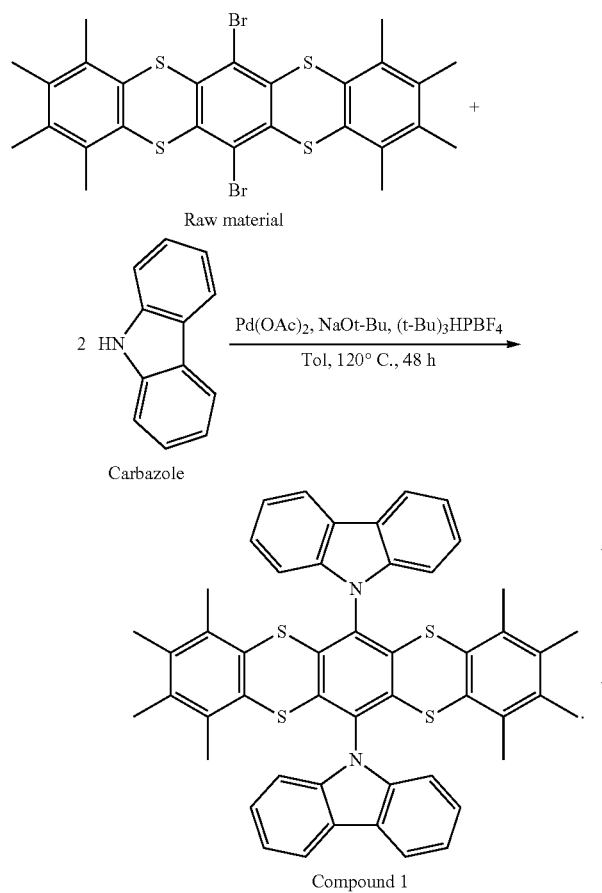

Compound 1

Embodiment 4

The Preparing Method of Compound 2:

Add raw materials (3.11 g, 5 mmol), diphenylamine (2.02 g, 12 mmol), palladium acetate (180 mg, 0.8 mmol) and tri-tert-butylphosphine tetrafluoroborate (0.68 g, 2.4 mmol) to a 250 mL two-necked flask, and then add sodium tert-butoxide (1.16 g, 12 mmol) to the two-necked flask in a glove box. Under an argon atmosphere, add 100 mL toluene which removes water and oxygen to the two-necked flask and react at 120° C. for 48 hours. After the reaction, cool the obtained reaction solution to room temperature and then pour the reaction solution into a 200 mL of ice water. The product is extracted from dichloromethane at least three times, combined with the organic phase, spun into silica gel, and then purified by column chromatography (volume ratio of dichloromethane and n-hexane is 1:4) to obtain a white powdery product (2.5 g, yield rate: 63%). The white powdery product confirmed by mass spectrometry (MS (EI) m/z: [M]+: 800.15) is Compound 2.

Wherein the preparation route of Compound 2 is as following:

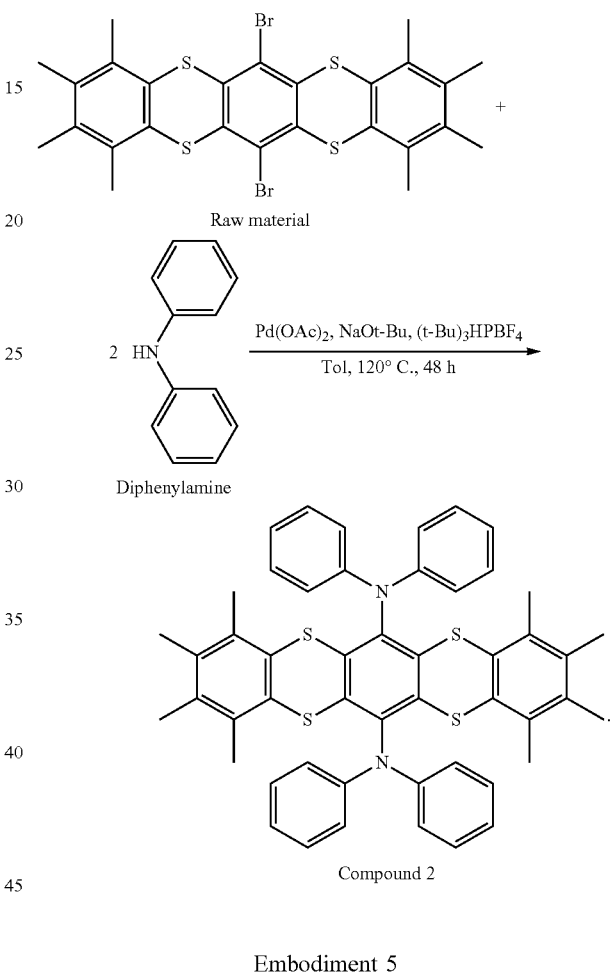

Compound 2

Embodiment 5

The Preparing Method of Compound 3:

Add raw materials (3.11 g, 5 mmol), 9,9'-dimethyl acridine (2.50 g, 12 mmol), palladium acetate (180 mg, 0.8 mmol) and tri-tert-butylphosphine tetrafluoroborate (0.68 g, 2.4 mmol) to a 250 mL two-necked flask, and then add sodium tert-butoxide (1.16 g, 12 mmol) to the two-necked flask in a glove box. Under an argon atmosphere, add 100 mL toluene which removes water and oxygen to the two-necked flask and react at 120° C. for 48 hours. After the reaction, cool the obtained reaction solution to room temperature and then pour the reaction solution into a 200 mL of ice water. The product is extracted from dichloromethane at least three times, combined with the organic phase, spun into silica gel, and then purified by column chromatography (volume ratio of dichloromethane and n-hexane is 1:4) to obtain a white powdery product (3.1 g, yield rate: 70%). The white powdery product confirmed by mass spectrometry (MS (EI) m/z: [M]+: 880.21) is Compound 3.

Wherein the preparation route of Compound 3 is as following:

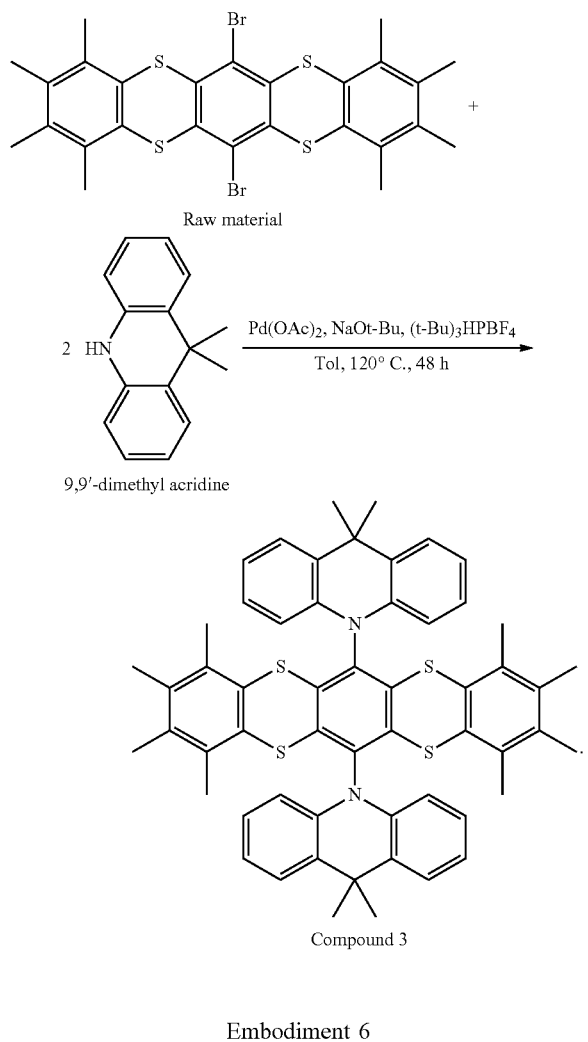

Compound 3

Embodiment 6

The Preparing Method of Compound 4:

(1) Add raw materials (3.11 g, 5 mmol), carbazole (1.00 g, 6 mmol), palladium acetate (90 mg, 0.4 mmol) and tri-tert-butylphosphine tetrafluoroborate (0.34 g, 1.2 mmol) to a 250 mL two-necked flask, and then add sodium tert-butoxide (0.58 g, 6 mmol) to the two-necked flask in a glove box. Under an argon atmosphere, add 100 mL toluene which removes water and oxygen to the two-necked flask and react at 120° C. for 48 hours. After the reaction, cool the obtained reaction solution to room temperature and then pour the reaction solution into a 200 mL of ice water. The product is extracted from dichloromethane at least three times, combined with the organic phase, spun into silica gel, and then purified by column chromatography (volume ratio of dichloromethane and n-hexane is 1:4) to obtain a white powdery product (2.8 g, yield rate: 79%). The white powdery product confirmed by mass spectrometry (MS (EI) m/z: [M]+: 709.12) is Intermediate product 1;

(2) Add the Intermediate product 1 (3.55 g, 5 mmol), diphenylamine (1.01 g, 6 mmol), palladium acetate (90 mg, 0.4 mmol) and tri-tert-butylphosphine tetrafluoroborate (0.34 g, 1.2 mmol) to a 250 mL two-necked flask, and then add sodium tert-butoxide (0.58 g, 6 mmol) to the two-necked flask in a glove box. Under an argon atmosphere, add 100 mL toluene which removes water and oxygen to the two-necked flask and react at 120° C. for 48 hours. After the reaction, cool the obtained reaction solution to room temperature and then pour the reaction solution into a 200 mL of ice water. The product is extracted from dichloromethane at least three times, combined with the organic phase, spun into silica gel, and then purified by column chromatography (volume ratio of dichloromethane and n-hexane is 1:4) to obtain a white powdery product (3.0 g, yield rate: 75%). The white powdery product confirmed by mass spectrometry (MS (EI) m/z: [M]+: 798.03) is Compound 4.

Wherein the preparation route of Compound 4 is as following:

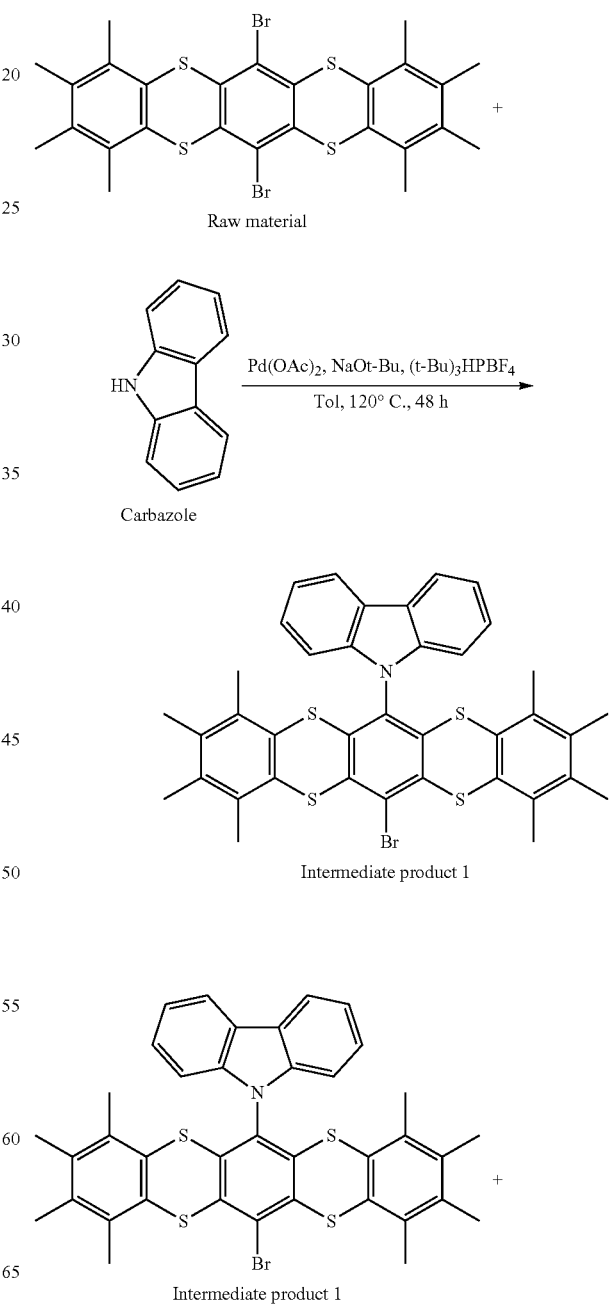

-continued

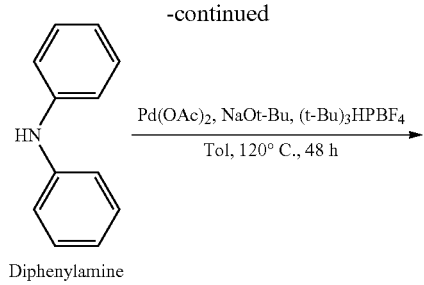

Diphenylamine

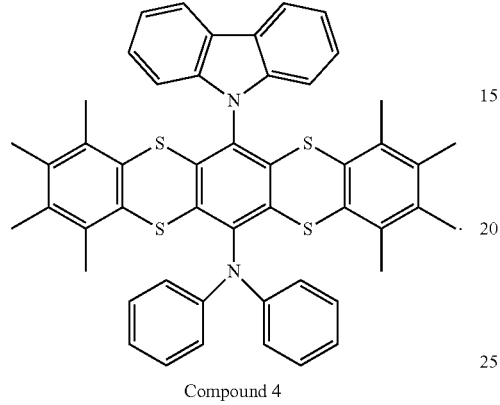

Compound 4

Embodiment 7

The Preparing Method of Compound 5:

(1) Add raw materials (3.11 g, 5 mmol), carbazole (1.00 g, 6 mmol), palladium acetate (90 mg, 0.4 mmol) and tri-tert-butylphosphine tetrafluoroborate (0.34 g, 1.2 mmol) to a 250 mL two-necked flask, and then add sodium tert-butoxide (0.58 g, 6 mmol) to the two-necked flask in a glove box. Under an argon atmosphere, add 100 mL toluene which removes water and oxygen to the two-necked flask and react at 120° C. for 48 hours. After the reaction, cool the obtained reaction solution to room temperature and then pour the reaction solution into a 200 mL of ice water. The product is extracted from dichloromethane at least three times, combined with the organic phase, spun into silica gel, and then purified by column chromatography (volume ratio of dichloromethane and n-hexane is 1:4) to obtain a white powdery product (2.8 g, yield rate: 79%). The white powdery product confirmed by mass spectrometry (MS (EI) m/z: [M]+: 709.12) is Intermediate product 1;

(2) Add the Intermediate product 1 (3.55 g, 5 mmol), 9,9'-dimethyl acridine (1.25 g, 6 mmol), palladium acetate (90 mg, 0.4 mmol) and tri-tert-butylphosphine tetrafluoroborate (0.34 g, 1.2 mmol) to a 250 mL two-necked flask, and then add sodium tert-butoxide (0.58 g, 6 mmol) to the two-necked flask in a glove box. Under an argon atmosphere, add 100 mL toluene which removes water and oxygen to the two-necked flask and react at 120° C. for 48 hours. After the reaction, cool the obtained reaction solution to room temperature and then pour the reaction solution into a 200 mL of ice water. The product is extracted from dichloromethane at least three times, combined with the organic phase, spun into silica gel, and then purified by column chromatography (volume ratio of dichloromethane and n-hexane is 1:4) to obtain a white powdery product (2.8 g, yield rate: 67%). The white powdery product confirmed by mass spectrometry (MS (EI) m/z: [M]+: 839.19) is Compound 5.

Wherein the preparation route of Compound 5 is as following:

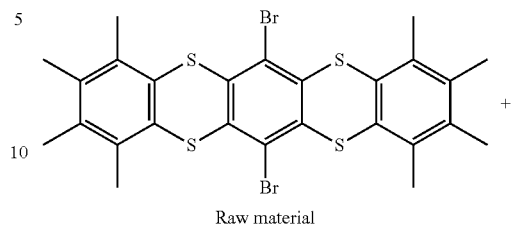

Raw material

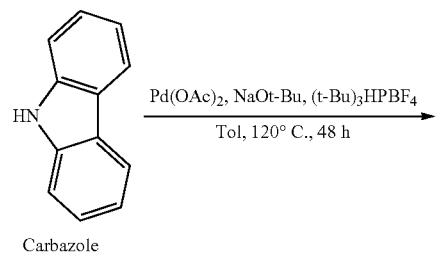

Carbazole

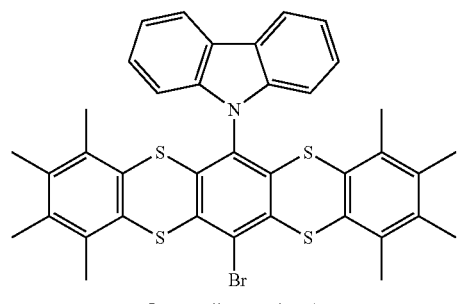

Intermediate product 1

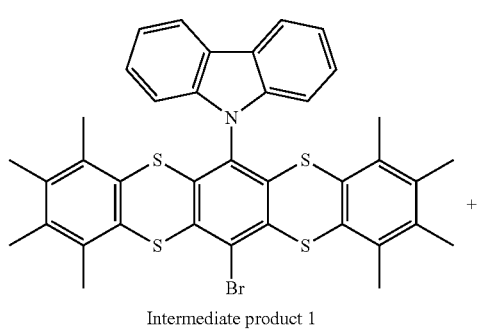

Intermediate product 1

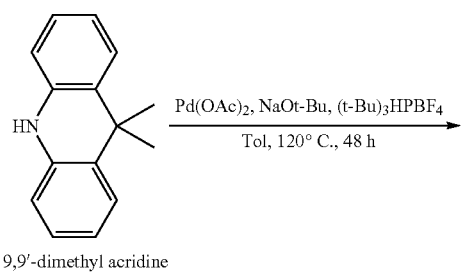

9,9'-dimethyl acridine

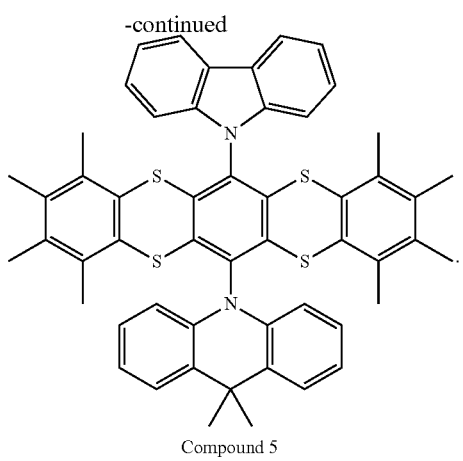

Compound 5

Embodiment 8

The Preparing Method of Compound 6:

(1) Add raw materials (3.11 g, 5 mmol), diphenylamine (1.01 g, 6 mmol), palladium acetate (90 mg, 0.4 mmol) and tri-tert-butylphosphine tetrafluoroborate (0.34 g, 1.2 mmol) to a 250 mL two-necked flask, and then add sodium tert-butoxide (0.58 g, 6 mmol) to the two-necked flask in a glove box. Under an argon atmosphere, add 100 mL toluene which removes water and oxygen to the two-necked flask and react at 120° C. for 48 hours. After the reaction, cool the obtained reaction solution to room temperature and then pour the reaction solution into a 200 mL of ice water. The product is extracted from dichloromethane at least three times, combined with the organic phase, spun into silica gel, and then purified by column chromatography (volume ratio of dichloromethane and n-hexane is 1:4) to obtain a white powdery product (2.6 g, yield rate: 73%). The white powdery product confirmed by mass spectrometry (MS (EI) m/z: [M]+: 711.01) is Intermediate product 2;

(2) Add the Intermediate product 2 (3.56 g, 5 mmol), 9,9'-dimethyl acridine (1.25 g, 6 mmol), palladium acetate (90 mg, 0.4 mmol) and tri-tert-butylphosphine tetrafluoroborate (0.34 g, 1.2 mmol) to a 250 mL two-necked flask, and then add sodium tert-butoxide (0.58 g, 6 mmol) to the two-necked flask in a glove box. Under an argon atmosphere, add 100 mL toluene which removes water and oxygen to the two-necked flask and react at 120° C. for 48 hours. After the reaction, cool the obtained reaction solution to room temperature and then pour the reaction solution into a 200 mL of ice water. The product is extracted from dichloromethane at least three times, combined with the organic phase, spun into silica gel, and then purified by column chromatography (volume ratio of dichloromethane and n-hexane is 1:4) to obtain a white powdery product (2.5 g, yield rate: 72%). The white powdery product confirmed by mass spectrometry (MS (EI) m/z: [M]+: 838.20) is Compound 6.

Wherein the preparation route of Compound 6 is as following:

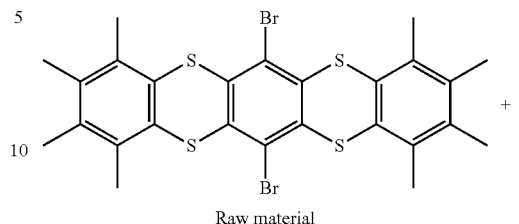

Raw material

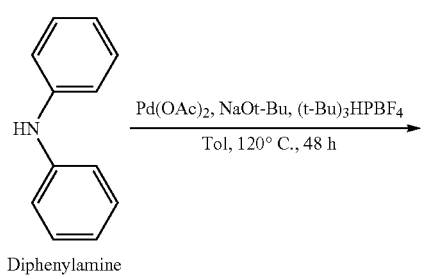

Diphenylamine

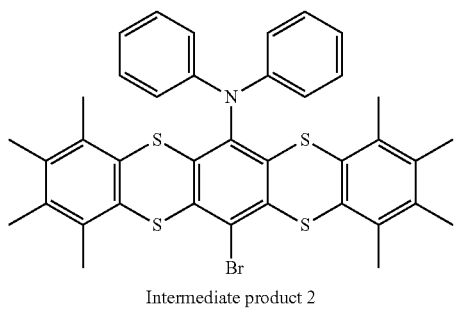

Intermediate product 2

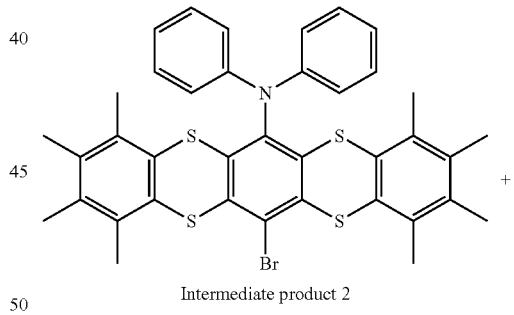

Intermediate product 2

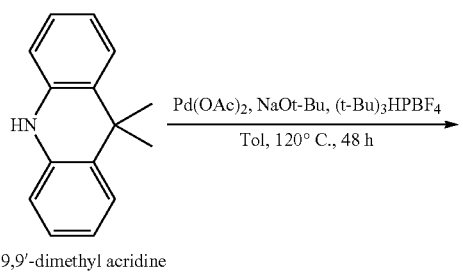

9,9'-dimethyl acridine

-continued

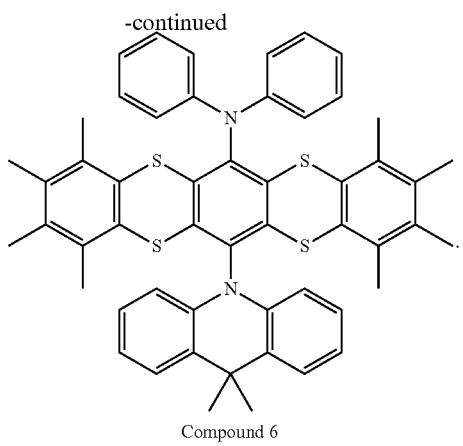

Compound 6

Embodiment 9

As shown in the FIGURE, an embodiment of the present disclosure provides an organic light-emitting device 100, comprising an anode 10, a hole injection layer 20, a hole transport layer 30, a light-emitting layer 40, an electron transport layer 50, an electron injection layer 60 and a cathode 70. Wherein the material of the hole transport layer 30 comprises above dithiazine-based hole transport material, such as Compound 1, Compound 2, Compound 3, Compound 4, Compound 5 or Compound 6.

Table 1 shows electrochemical energy levels of Compound 1, Compound 2, Compound 3, Compound 4, Compound 5 and Compound 6.

TABLE 1

|  | HOMO (eV) | LUMO (eV) |
| --- | --- | --- |
| Compound 1 | −5.58 | −2.63 |
| Compound 2 | −5.64 | −2.63 |
| Compound 3 | −5.66 | −2.63 |
| Compound 4 | −5.60 | −2.63 |
| Compound 5 | −5.62 | −2.63 |
| Compound 6 | −5.65 | −2.63 |

As shown in table 1, the six compound provided in embodiment 2 to embodiment 8 have the same LUMO energy level. This is because the LUMO of the above six compounds is distributed on the same central core (the dithiazine structure), and the HOMOs of the compounds are distributed on the electron-donating groups of carbazolyl group, diphenylamino group or 9,9'-dimethyl acridine group. Due to different electron-donating abilities of the electron-donating groups, the energy levels of compound 1 to 6 show differences. The performance of electron-donating abilities is 9,9'-dimethyl acridine group≈diphenylamino group>carbazolyl group. Therefore, the performance of HOMO energy levels of the above six compounds is Compound 3≈Compound 6≈Compound 2>Compound 5>Compound 4>Compound 1, and HOMO energy levels of above six compounds are around −5.6 eV which match the HOMO energy level (−5.50 eV) of a P-type doped hole transport material. It proves that the energy levels of Compound 1 to Compound 6 provided in embodiment 2 to embodiment 8 match the energy levels of a hole transport material.

Table 2 shows the hole transport properties of the corresponding organic light-emitting devices (referred to as device in the table) when Compound 1 to Compound 6 are used as the material of the hole transport layer respectively.

TABLE 2

| Device | Hole transport layer | The highest current efficiency (cd/A) | $(CIE_x, CIE_y)$ | Maximum external quantum efficiency (%) |
| --- | --- | --- | --- | --- |
| Device 1 | Compound 1 | 6.0 | (0.13, 0.044) | 13.3% |
| Device 2 | Compound 2 | 5.8 | (0.13, 0.046) | 12.5% |
| Device 3 | Compound 3 | 5.7 | (0.13, 0.045) | 12.1% |
| Device 4 | Compound 4 | 5.9 | (0.13, 0.044) | 13.0% |
| Device 5 | Compound 5 | 5.8 | (0.13, 0.046) | 12.7% |
| Device 6 | Compound 6 | 5.7 | (0.13, 0.045) | 12.3% |

As shown in table 2, the organic light-emitting devices prepared from the six compounds provided in embodiment 2 to 8 have better device properties (high hole mobilities). This is because the energy levels of these compounds are around −5.6 eV which match the HOMO energy level (−5.50 eV) of a P-type doped hole transport material. Meanwhile, it can be known from table 1 and table 2, with decreasing of HOMO energy level (Compound 3≈Compound 6≈Compound 2>Compound 5>Compound 4>Compound 1), the maximum external quantum efficiency of the device is gradually increasing (Compound 1>Compound 4>Compound 5>Compound 2>Compound 6>Compound 3).

The present disclosure has been described with a preferred embodiment thereof. The preferred embodiment is not intended to limit the present disclosure, and it is understood that many changes and modifications to the described embodiment can be carried out without departing from the scope and the spirit of the disclosure that is intended to be limited only by the appended claims.

What is claimed is:

1. A dithiazine-based hole transport material, comprising a molecular structural formula as following:

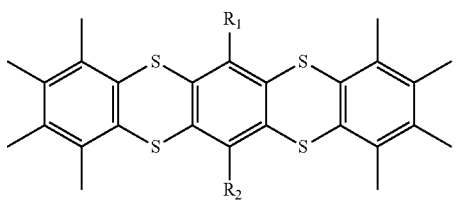

wherein $R_1$ and $R_2$ are each a carbazolyl group and derivatives thereof, a diphenylamino group and derivatives thereof, a phenazine group and derivatives thereof, an acridine group and derivatives thereof, or a five-membered or six-membered heterocyclic aromatic group having one or more hetero atoms selected from the group consisting of N, O and Si.

2. The dithiazine-based hole transport material according to claim 1, wherein $R_1$ and $R_2$ are each a substituted or unsubstituted dialkylamino group, substituted or unsubstituted alkylamino group, substituted or unsubstituted amino group, substituted or unsubstituted alkoxy group, substituted or unsubstituted amide group, substituted or unsubstituted acyloxy group, substituted or unsubstituted alkyl group, substituted or unsubstituted carboxymethyl group, substituted or unsubstituted phenyl group or hydroxyl group; wherein the substituted group is an alkyl group or halogen.

3. The dithiazine-based hole transport material according to claim 1, wherein $R_1$ and $R_2$ are each a structural formula selected from the group consisting of following structural formulas:

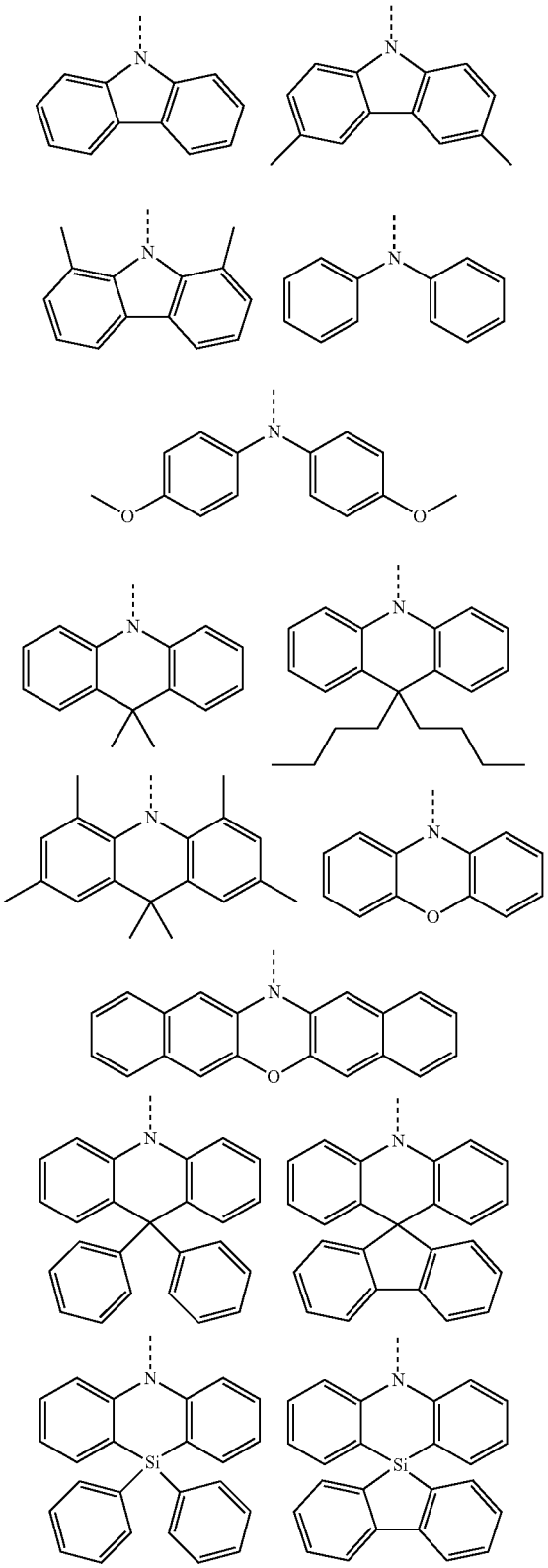

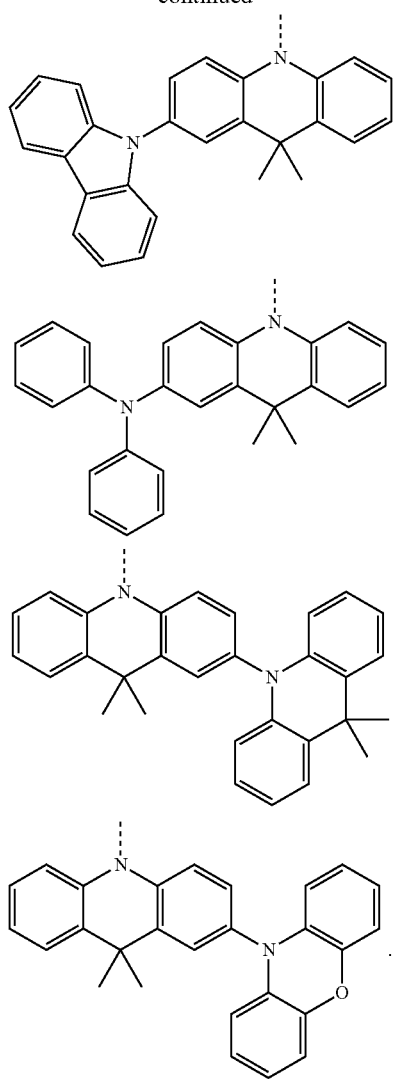

4. The dithiazine-based hole transport material according to claim 1, wherein $R_1$ and $R_2$ are the same.

5. The dithiazine-based hole transport material according to claim 1, wherein a molecular structural formula of the dithiazine-based hole transport material is selected from the group consisting of following structural formulas:

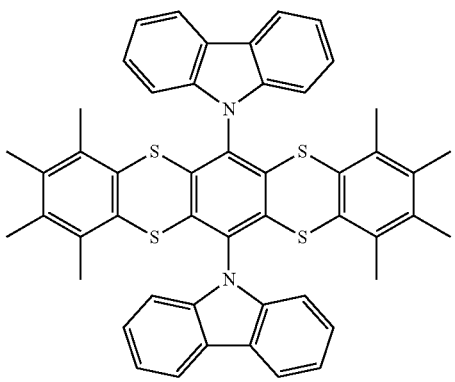

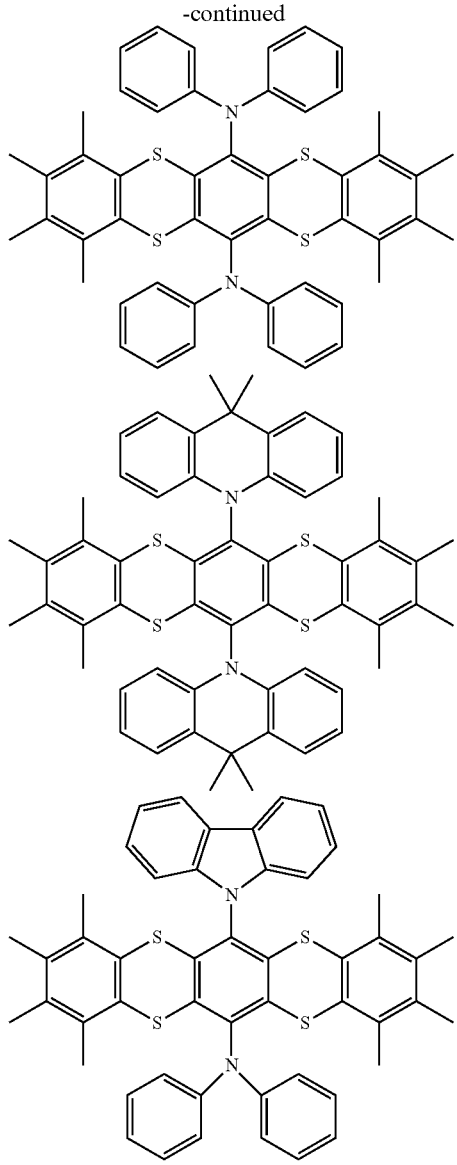
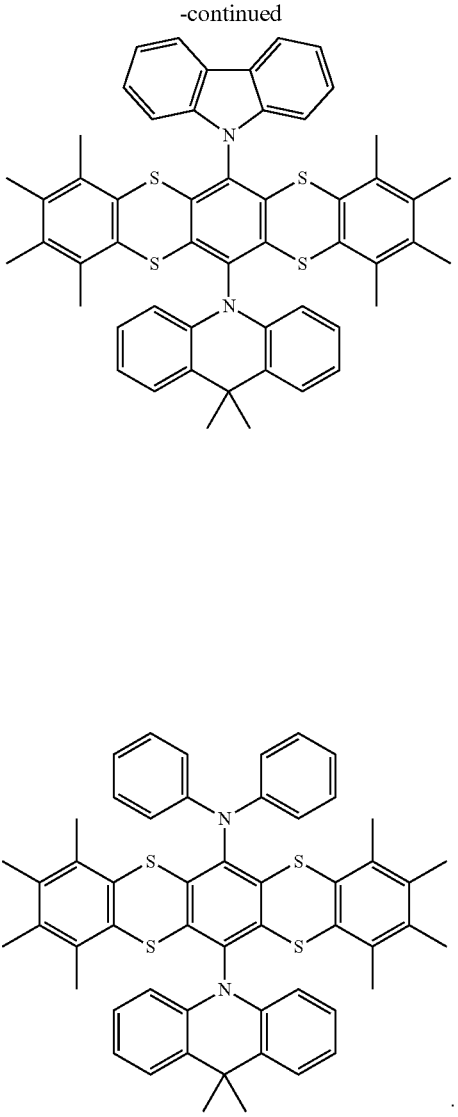
* * * * *